United States Patent [19]
Johansson et al.

[11] Patent Number: 5,686,464
[45] Date of Patent: *Nov. 11, 1997

[54] 3,3-DIPHENYLPROPYLAMINES, THEIR USE AND PREPARATION

[75] Inventors: Rolf Arne Johansson, Huddinge; Pinchas Moses, Satsjö-Boo; Lisbeth Nilvebrant, Bromma; Bengt Åke Sparf, Trångsund, all of Sweden

[73] Assignee: Pharmacia AB, Stockholm, Sweden

[*] Notice: The term of this patent shall not extend beyond the expiration date of Pat. No. 5,559,269.

[21] Appl. No.: 684,638

[22] Filed: Jul. 22, 1996

Related U.S. Application Data

[62] Division of Ser. No. 432,113, filed as PCT/SE93/00927 Nov. 5, 1993, published as WO94/11337 May 26, 1994, Pat. No. 5,559,269.

[30] Foreign Application Priority Data

Nov. 6, 1992 [SE] Sweden ............ 9203318

[51] Int. Cl.[6] ............ A61K 31/135
[52] U.S. Cl. ............ 514/315; 514/317; 514/408; 514/648; 546/216; 546/240; 546/242; 546/248; 548/541; 548/556; 548/574; 548/575; 548/578; 564/443
[58] Field of Search ............ 564/443; 514/315, 514/317, 408, 648; 546/216, 240, 242, 248; 548/541, 556, 574, 575, 578

[56] References Cited

U.S. PATENT DOCUMENTS 5,559,269  9/1996  Johansson et al. ............ 564/443

FOREIGN PATENT DOCUMENTS 1216318  11/1962  Germany .
1169944  11/1969  United Kingdom .
1169945  11/1969  United Kingdom .
9411337   5/1994  WIPO .

*Primary Examiner*—Frederick Krass
*Attorney, Agent, or Firm*—Birch, Stewart, Kolasch & Birch, LLP

[57] ABSTRACT

A 3,3-diphenylpropylamine of the formula I, or its physiologically acceptable acid salt thereof:

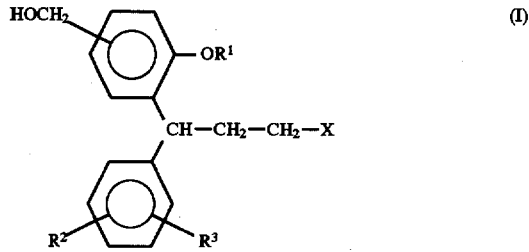

wherein $R^1$ represents hydrogen or methyl, $R^2$ and $R^3$ independently represent hydrogen, methyl, methoxy, hydroxy, carbamoyl, sulphamoyl or halogen, and X represents a tertiary amino group of formula II

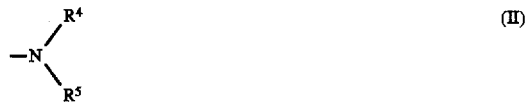

wherein $R^4$ and $R^5$ independently represent a hydroxy substituted or unsubstituted non-aromatic hydrocarbyl group which can join together to form a ring and which together contain at least three carbon atoms, wherein at least one of $R^4$ and $R^5$ is hydroxy substituted, is useful in treating acetylcholine-mediated disorders such as urinary incontinence.

10 Claims, 1 Drawing Sheet

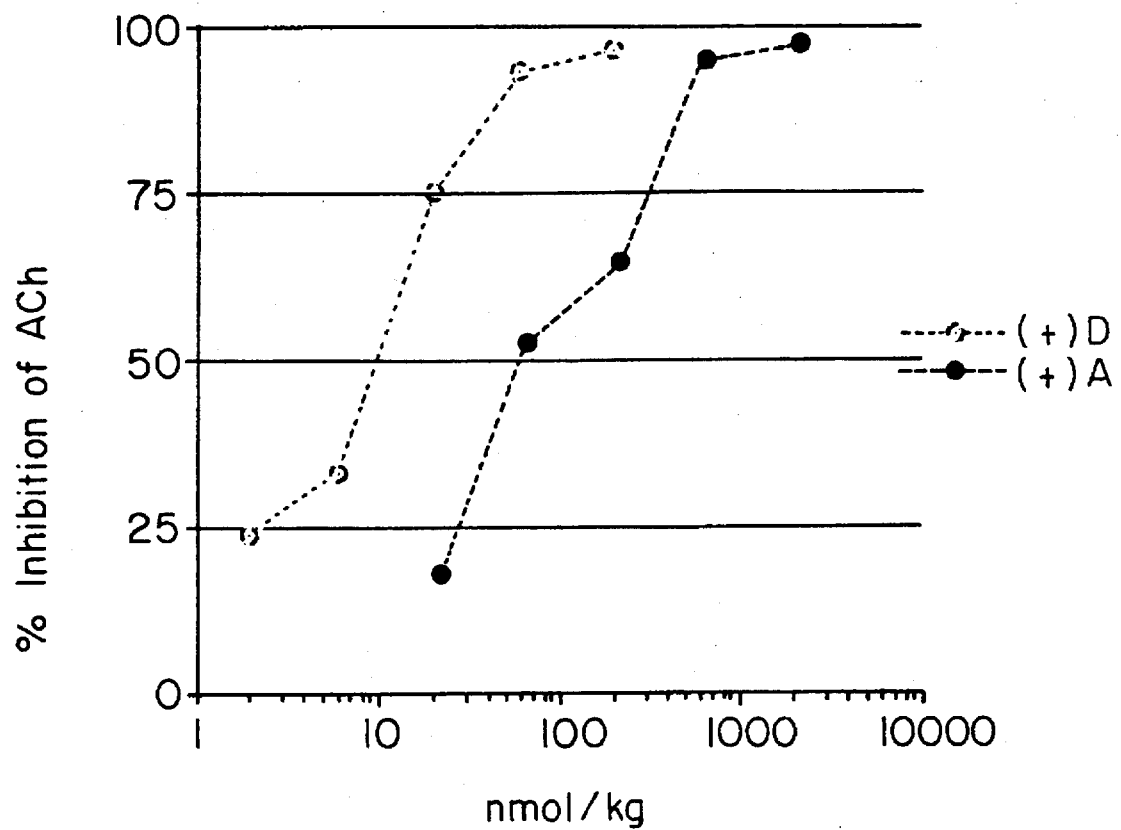

3,3-DIPHENYLPROPYLAMINES, THEIR USE AND PREPARATION

This application is a divisional of application Ser. No. 08/432,113, filed as PCT/SE93/00927 Nov, 5, 1993, published as WO94/11337 May 26, 1994 now U.S. Pat. No. 5,559,269 the entire contents of which are hereby incorporated by reference.

The present invention relates to novel therapeutically active compounds, methods for their preparation, pharmaceutical compositions containing the novel compounds, and the use of the compounds for preparing drugs.

WO 89/06644 discloses 3,3-diphenylpropylamines having anticholinergic activity. In accordance with the present invention novel therapeutically active compounds have now been found, some of which are formed as metabolites in mammals when treated with the 3,3-diphenylpropylamines disclosed in the above-mentioned WO publication. These metabolites have at least as favourable anti-cholinergic properties as the parent compounds and can thus be used for the control of events mediated by .acetylcholine, like urination.

The novel compounds of the present invention are represented by the general formula I

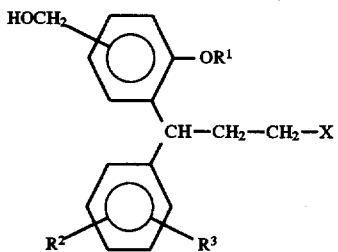

I wherein $R^1$ signifies hydrogen or methyl, $R^2$ and $R^3$ independently signify hydrogen, methyl, methoxy, hydroxy, carbamoyl, sulphamoyl or halogen, and X represents a tertiary amino group of formula II

II wherein $R^4$ and $R^5$ signify non-aromatic hydrocarbyl groups, which may be the same or different and which together contain at least three carbon atoms, preferably at least four carbon atoms, especially at least five carbon atoms, and wherein $R^4$ and $R^5$ may form a ring together with the amine nitrogen, said ring preferably having no other heteroatom than the amine nitrogen.

The compounds of formula I can form salts with physiologically acceptable acids, organic and inorganic, and the invention comprises the free bases as well as the salts thereof. Examples of such acid addition salts include the hydrochloride, hydrobromide, hydrogen fumarate, and the like.

When the novel compounds are in the form of optical isomers, the invention comprises the racemic mixture as well as the individual isomers as such.

In the compounds of formula I, $R^2$ is preferably hydrogen and $R^3$ is preferably hydrogen or hydroxy.

$R^2$ is preferably in 3-, 4- or 5-position.

$R^3$ is preferably in 2-position with respect to the propylamine group.

The $HOCH_2$-group is preferably in 5-position.

Preferably, each of $R^4$ and $R^5$ independently signifies $C_{1-8}$-alkyl, especially $C_{1-6}$-alkyl, or adamantyl, $R^4$ and $R^5$ together comprising at least three, preferably at least four carbon atoms. $R^4$ and $R^5$ may carry one or more hydroxy groups, and they may be joined to form a ring together with the amine nitrogen atom.

Presently preferred tertiary amino groups X in formula I include the following groups a)–h):

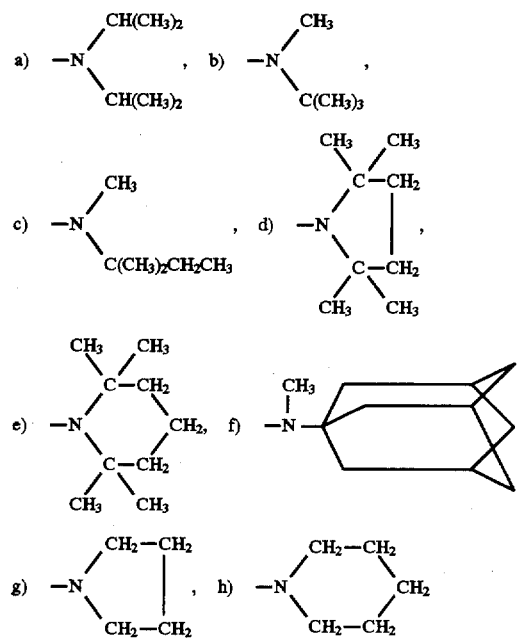

Preferably, $R^4$ and $R^5$ are both isopropyl.

A presently preferred specific compound of formula I is N,N-diisopropyl-3-(2-hydroxy-5-hydroxymethylphenyl)-3-phenylpropylamine.

The compounds of formula I may, in accordance with the present invention, be prepared by per se conventional methods, and especially by a) reducing the group $R^6CO$ in a 3,3-diphenylpropylamine of formula III

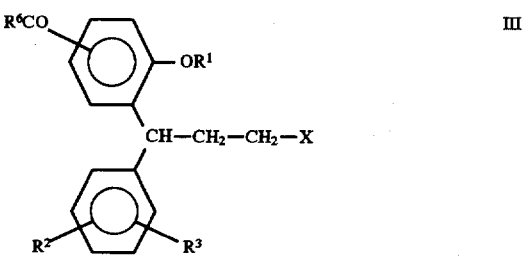

III wherein $R^1$ to $R^3$ and X are as defined above, $R^6$ is hydrogen or $R^7O$, where $R^7$ is hydrogen, (preferably lower) alkyl, alkenyl, alkynyl or aryl (such as phenyl) and any hydroxy groups may be protected, such as by methylation or benzylation, or b) reacting a reactively esterified 3,3-diphenylpropanol of formula IV

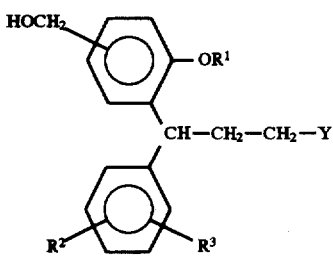

wherein $R^1$ to $R^3$ are as defined above and any hydroxy groups may be protected, and wherein Y is a leaving group, preferably halogen or an alkyl or arylsulphonyloxy group, with an amine of formula V

H—X  V wherein X is as defined above, or c) reducing a 3,3-diphenylpropionamide of formula VI

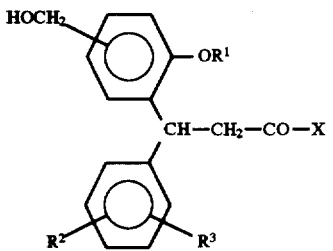

wherein $R^1$ to $R^3$ and X are as defined above and any hydroxy groups may be protected, preferably using a complex metal hydride, or d) N-methylating a secondary 3,3-diphenylpropylamine of formula VII

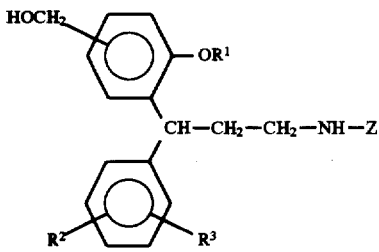

wherein $R^1$ to $R^3$ and X are as defined above and any hydroxy groups may be protected, and wherein Z has the same meaning as $R^4$ and $R^5$ with the exception of methyl, Z preferably being a hydrocarbyl group comprising at least three carbon atoms, the N-methylation preferably being carried out using formaldehyde or formic acid, or e) reducing a 3,3-diphenylpropenamine of formula VIIIa or a 3,3-diphenylpropylamine of formula VIIIb

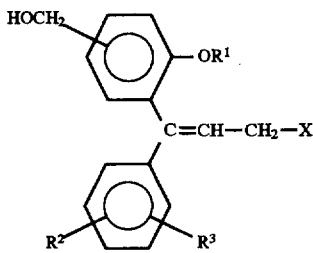

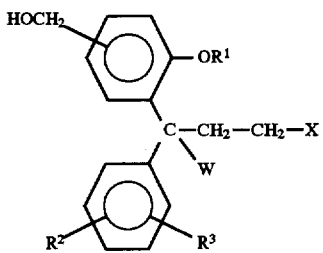

wherein $R^1$ to $R^3$ and X are as defined above and any hydroxy groups may be protected, and W signifies a hydroxy group or a halogen atom, preferably by means of catalytic hydrogenation, f) reacting a 3,3-diphenylpropylamine of formula IX

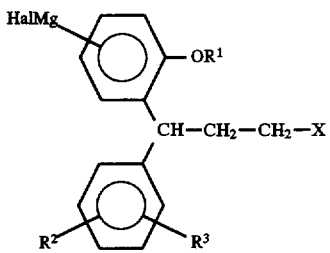

wherein $R^1$ to $R^3$ and X are as defined above, and Hal is halogen, with formaldehyde or a formaldehyde equivalent (such as s-trioxane), or g) oxidizing the methyl group of a diphenylpropylamine of formula X

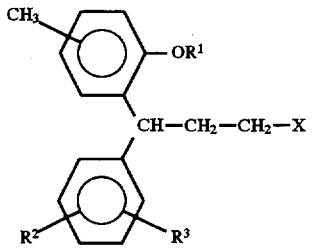

wherein $R^1$ to $R^3$ and X are as defined above, and
i) when necessary splitting off hydroxy protecting groups in the compounds obtained, if desired after mono- or di-halogenation of one or both of the phenyl rings, and/or
ii) if desired converting the obtained bases of formula I into salts thereof with physiologically acceptable acids, or vice versa, and/or iii) if desired separating an obtained mixture of optical isomers into the individual enantiomers, and/or iv) if desired methylating an ortho-hydroxy group in an obtained compound of formula I, wherein $R^1$ is hydrogen and/or $R^3$ is hydroxy.

The oxidation in process g) above may be performed chemically, electrochemically or enzymatically. Chemical oxidation is advantageously performed using a metal salt or oxide like ceric ammonium nitrate, manganese oxides, chromium oxides, vanadinium oxides, cobalt acetate, aluminium oxide, bismuth molybdate or combinations thereof. Chemical oxidation may also be effected by peracids, with or without a catalyst, or with halides. Electrochemical oxidation may be conducted with or without a catalyst. For enzymatical oxidation, it is preferred to use bacteria or yeast (e.g. Candida Guilliermondi, Candida Tropicalis).

The removal of hydroxy protecting groups according to i) above can e.g. be done by treatment with hydrobromic acid, borontribromide or by catalytic hydrogenation.

The separation of mixtures of optical isomers, according to ii) above, into the individual enantiomers can e.g. be achieved by fractional crystallization of salts with chiral acids or by chromatographic separation on chiral columns.

The starting compounds of formula III and IX may be prepared as described in the preparation example described below. The starting materials used in processes b) to e) and g) may be prepared as described in the afore-mentioned WO 89/06644 (the disclosure of which is incorporated by reference herein) with due consideration of the disclosure in the present preparation example.

In accordance with the present invention, the compounds of formula I, in the form of free bases or salts with physiologically acceptable acids, can be brought into suitable galenic forms, such as compositions for oral use, for injection, for nasal spray administration or the like, in accordance with accepted pharmaceutical procedures. Such pharmaceutical compositions according to the invention comprise an effective amount of the compounds of formula I in association with compatible pharmaceutically acceptable carrier materials, or diluents, as is well known in the art. The carriers may be any inert material, organic or inorganic, suitable for enteral, percutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmaceutically active agents, and conventional additives, such as stabilizers, wetting agents, emulsifiers, flavouring agents, buffers, and the like.

The compositions according to the invention can e.g. be made up in solid or liquid form for oral administration, such as tablets, capsules, powders, syrups, elixirs and the like, in the form of sterile solutions, suspensions or emulsions for parenteral administration, and the like.

The compounds and compositions can, as mentioned above, be used for the same therapeutical indications as the compounds of the above-mentioned WO 89/06644, i.e. for the treatment of acetylcholine-mediated disorders, such as urinary incontinence. The dosage of the specific compound will vary depending on its potency, the mode of administration, the age and weight of the patient and the severity of the condition to be treated. The daily dosage may, for example, range from about 0.01 mg to about 4 mg per kilo of body weight, administered singly or multiply in doses e.g. from about 0.05 mg to about 200 mg each.

The invention will be further illustrated by the following non-limiting example and pharmacological tests. Reference will be made to the accompanying drawing where the only figure (FIG. 1) shows bladder pressure inhibition curves for a compound of the present invention and a prior art compound, respectively.

FIG. 1 shows the dose-dependent inhibition of the acetylcholine-induced effect on the bladder by N,N-diisopropyl-3 (2-hydroxy-5-hydroxymethylphenyl)-3-phenylpropylamine(−) mandeli acid salt.

GENERAL

N.M.R data were acquired on a Jeol JNM-EX 270 Fourier transform spectrometer. Spectra were recorded with tetramethylsilane (TMS) as internal standard at 30° C. Infrared spectra were recorded on a Perkin Elmer 599B instrument. Non-corrected melting points were obtained on a Koeffler apparatus. Gas chromatography was performed on a HP 5940 instrument with a 10 m HP-1 column and the oven heated in the linear temperature gradient mode.

EXAMPLE 1

(+)-N,N-Diisopropyl-3-(2-hydroxy-5-hydroxymethyphenyl)-3-phenylpropylamine (+) mandelate, and (−)-N,N-diisopropyl-3-(2-hydroxy-5-hydroxymethylphenyl)-3-phenylpropylamine (−) mandelate a) 6-Bromo-4-phenyl-3,4-dihydro-coumarine

A solution of p-bromophenol (138 g, 0.8 mole), cinnamic acid (148 g, 1.0 mole), acetic acid (200 g) and conc. sulfuric acid was refluxed for 2 h. Volatile material was distilled at reduced pressure. The residual syrup was cooled and triturated with cold water, giving a semi-crystalline mass. This was washed extensively with water, saturated sodium carbonate and finally with water again. The material was filtered through a sintered glass funnel, and then mixed with an equal weight of ethanol. The slurry was stirred at room temperature for 1 h and then filtered. The resulting product was washed briefly with ethanol and then diisopropyl ether. After drying, 135 g (55.7%) of the title compound was isolated as white crystals, melting at 117° C.

b) Methyl 3-(2-benzyloxy-5-bromophenyl)-3-phenylpropanonate

6-Bromo-4-phenyl-3,4-dihydro-coumarine (290 g, 0.96 mole) was dissolved in a mixture of methanol (1 L) and acetone (1 L). To the above solution were added potassium carbonate (160 g, 1.16 mole), α-chlorotoluene (140 g, 1.1 mole) and sodium iodide (30 g, 0.47 mole), and the mixture was stirred under reflux for 3 h. The solution was concentrated by distillation, and the residue treated with water and extracted with diethyl ether. The ethereal layer was washed with water, saturated sodium carbonate solution and water, successively. The organic layer was dried over sodium sulfate, filtered and then evaporated to give 420 g (≈100%) of the title compound as a light yellow oil.

c) 3-(2-benzyloxy-5-bromophenyl)-3-phenylpropanol

Methyl 3-(2-benzyloxy-5-bromophenyl)-3-phenylpropanonate (112 g, 0.26 mole) was dissolved in tetrahydrofuran (250 mL) and added dropwise under nitrogen atmosphere to a suspension of lithium aluminiumhydride (5.9 g, 0.16 mole) in tetrahydrofuran (250 mL). The mixture was stirred overnight under nitrogen atmosphere. The excess hydride was decomposed by addition of a small amount of HCl (aq, 2M). The solution was filtered on a pad of Celatom, and the solids were washed thoroughly with ether. The combined ethereal solution was washed with HCl (2M), water, sodium hydroxide (2M) and then with water again. The organic solution was dried over sodium sulfate, filtered and evaporated to give 98.5 g (95%) of the title compound as a colourless oil. A small fraction of the oil was crystallized from diisopropyl ether/petroleum ether giving crystals which melted at 70° C.

d) 3-(2-benzyloxy-5-bromophenyl)-3-phenylpropyl-p-toluenesulfonate

To a solution of 3-(2-benzyloxy-5-bromophenyl)-3-phenylpropanol (107 g, 0.24 mole) in dichloromethane (300 mL) and pyridine (75 mL) at 0° C. was added p-toluene sulfonylchloride (57 g, 0.3 mole). The solution was stirred at 0° C. overnight and then evaporated at reduced pressure and at a bath temperature below 50° C. The remainder was poured onto water and then the mixture was extracted with diethyl ether. The organic layer was washed with water, HCl (2M) and water successively, and finally dried over sodium sulfate. After filtration the ethereal solution was evaporated at a bath temperature of <50° C. giving 137 g (≈100%) of 3-(2-benzyloxy-5-bromophenyl)-3-phenylpropyl-p-toluenesulfonate as a pale yellow oil.

e) N,N-Diisopropyl-3-(2-benzyloxy-5-bromophenyl)-3-phenylpropylamine 3-(2-benzyloxy-5-bromophenyl)-3-phenylpropyl-p-toluenesulfonate (115 g, 0.2 mole) was dissolved in a mixture of acetonitrile (150 g) and diisopropylamine (202 g, 2.0 mole) and the mixture was refluxed for 4 days. The solution was evaporated, and to the resulting syrup was added sodium hydroxide (2M, 200 mL). The mixture was concentrated, cooled and then extracted with diethyl ether. The ethereal layer was extensively washed with water. The amine was extracted with excess sulfuric acid (1M). The aqueous layer was washed with diethyl ether and then basified with sodium hydroxide (11M). The mixture was then extracted with diethyl ether. The organic layer was washed with water, dried over sodium sulfate, filtered and then evaporated to give 78.6 g (78%) of N,N-diisopropyl-3-(2-benzyloxy-5-bromophenyl)-3-phenylpropylamine as a pale yellow oil. The 1-H N.M.R spectrum was in accordance with the above structure.

f) Resolution

To a solution of N,N-diisopropyl-3-(2-benzyloxy-5-bromophenyl)-3-phenylpropylamine (255 g, 0.53 mole) in ethanol (750 g) was added L-(+)-tartaric acid (80 g, 0.53 mole). When all material was dissolved, diethyl ether (90 g) was added and crystallization commenced. After being stored at room temperature overnight, the formed salts were filtered off, washed with fresh ethanol-diethyl ether solution (2:1) and dried to give 98 g of white crystals melting at 156° C. [α]$^{22}$=16.3° (c=5.1, ethanol)

The mother liquor from the precipitation with L-(+)-tartaric acid was evaporated. The resulting syrup was treated with sodium hydroxide (2M) and extracted with diethyl ether. The organic phase was washed with water, dried over sodium sulfate, filtered and then evaporated, giving 170 g of free base. The base (170 g, 0.35 mole) was dissolved in ethanol (500 mL), and D-(−)-tartaric acid (53 g, 0.53 mole) was added. When all had dissolved, diethyl ether (50 mL) was added and crystallization commenced. The crystals were filtered off and washed with fresh ethanol-diethyl ether solution giving 105 g of crystals melting at 154°–155° C. [α]$^{22}$=−16.4° (c=5.0, methanol)

The mother liquor was concentrated, basified and treated as above, yielding 80 g of free base. This base was dissolved in ethanol, and treated with L-(+)-tartaric acid as described above, yielding additional 20 g of the dextrorotatory form of the salt. (M.p. 156° C.). In an analogous manner, 20 g of the levorotatory form could be obtained.

The pooled dextrorotatory form was dissolved in water and basified with sodium hydroxide (2M). The mixture was then extracted with diethyl ether. The organic phase was washed with water, dried over sodium sulfate, filtered and finally evaporated to give the chiral amine (88 g) as a colourless oil. [α]$^{22}$=16.3° (c=5.1, ethanol)

In an analogous fashion, the levorotatory base was obtained (90 g). [α]$^{22}$=−16.1° (c=4.2, ethanol). The optical purity as assessed by chromatography was >99%.

g1) (+)-N,N-Diisopropyl-3-(2-benzyloxy-5-carboxyphenyl)-3-phenylpropylamine hydrochloride A mixture of magnesium (12.2 g, 0.5 mole), ethyl bromide (2 g), and iodine (a small crystal) in dry diethyl ether (200 mL) was warmed until the reaction started. (+)-N,N-diisopropyl-3-(2-benzyloxy-5-bromophenyl)-3-phenylpropylamine (45.6 g, 0.095 mole) and ethyl bromide (32.7 g, 0.3 mole) dissolved in dry diethyl ether (250 mL) were then added dropwise under nitrogen atmosphere. The mixture was refluxed for 1.5 h and then cooled in an acetone/dry-ice bath, whereupon powdered dry ice (≈100 g) was added gently. Tetrahydrofuran was added when needed to prevent the mixture from solidification. The reaction mixture was stirred for 0.5 h when ammonium chloride (200 mL, 20% w/w) was added. The mixture was stirred vigorously until two transparent phases were formed, and then filtered through a pad of Celatom. The aqueous layer was washed with diethyl ether and then acidified with hydrochloric acid to pH 1. The precipitated semi-crystalline gum was washed with water, and then transferred to a round bottom flask. The product was dried by co-evaporation with acetone, benzene, toluene, diisopropyl ether and methanol, successively. The title compound (35.1 g, 77%) was isolated as friable shiny flakes and used without any further purification.

g2) (−)-N,N-Diisopropyl-3-(2-benzyloxy-5-carboxyphenyl)-3-phenylpropylamine hydrochloride This product was isolated in 81% yield in a corresponding way as described above from (−)-N,N-diisopropyl-3-(2-benzyloxy-5-bromophenyl)-3-phenylpropylamine.

h1) (+)-N,N-Diisopropyl-3-(2-benzyloxy-5-carbomethoxyphenyl)-3-phenylpropylamine (+)-N,N-Diisopropyl-3-(2-benzyloxy-5-carboxyphenyl)-3-phenylpropylamine (34 g, 0.07 mole) was dissolved in methanol (300 mL) containing sulfuric acid (6 g) and refluxed for 6 h. The solution was then cooled and concentrated. To the mixture were added ice-water and a slight excess of saturated sodium carbonate solution. The mixture was then extracted with diethyl ether. The organic phase was washed with water, dried over sodium sulfate, filtered and evaporated, giving 30 g (93%) of crude ester. Recrystallisation from diisopropyl ether gave white crystals melting at 85°–86° C. The 1-H N.M.R. spectrum was in accordance with the above structure.

h2) (−)-N,N-diisopropyl-3-(2-benzyloxy-5-carbomethoxyphenyl)-3-phenylpropylamine The title compound was obtained from (−)-N,N-diisopropyl-3-(2-benzyloxy-5-carboxyphenyl)-3- phenylpropylamine in a similar manner as described above for the dextro isomer in a 93% yield.

i1) (−)-N,N-Diisopropyl-3-(2-benzyloxy-5-hydroxymethylphenyl)-3-phenylpropylamine (+)-N,N-Diisopropyl-3-(2-benzyloxy-5-carbomethoxyphenyl)-3-phenylpropylamine (30 g, 0.065 mole) dissolved in diethyl ether (250 mL) was added dropwise under nitrogen to a suspension of lithium aluminiumhydride (1.9 g, 0.05 mole) in dry diethyl ether (150 mL). The mixture was stirred overnight at room temperature, and the excess hydride was decomposed by the addition of water (≈5 g). The mixture was stirred for 10 min, when sodium sulfate (s) was added. After stirring for 20 minutes, the mixture was filtered and then evaporated to give 28.4 g of the title compound as a colourless oil.

i2) (+)-N,N-Diisopropyl-3-(2-benzyloxy-5-hydroxymethylphenyl)-3-phenylpropylamine The title compound was obtained in an analogous fashion as described above for the levo isomer from (−)-N,N-diisopropyl-3-(2-benzyloxy-5-carbomethoxyphenyl)-3-phenylpropylamine.

j1) (+)-N,N-Diisopropyl-3-(2-hydroxy-5-hydroxymethylphenyl)-3-phenylpropylammonium (+) mandelate (+)-N,N-Diisopropyl-3-(2-benzyloxy-5-hydroxymethylphenyl)-3-phenylpropylamine (28.2 g, 0.065 mole) was dissolved in methanol (300 g). Raney Nickel (one teaspoon) was added and the mixture was hydrogenated at atmospheric pressure until the theoretical amount of hydrogen was consumed. The progress of the reaction was monitored by gas chromatography. The mixture was then filtered through a pad of Celatom, and the solvent was removed by evaporation at a bath temperature <50° C. The resulting oil was dissolved in diethyl ether, and the ethereal solution was washed with water, dried over sodium sulfate and evaporated giving 22.2 g of a colourless oil. $[\alpha]^{22}=16.7°$ (c=4.9, ethanol).

To the above oil, dissolved in 2-propanol (50 g) was added S-(+)-mandelic acid (9.6 g, 0.06 mole) in 2-propanol (50 g). Dry diethyl ether (50 g) was added, and the solution was left for several hours. The resulting heavy, white crystals were filtered off and washed with a mixture of 2-propanol and diethyl ether (1:1 v/v) and then dried, yielding 25 g of the title compound which melted at 148° C. $[\alpha]^{22}=38.3°$ (c=5.1, methanol).

The 1-H N.M.R. spectrum was in accordance with the above structure.

Chiral purity as assessed by H.P.L.C. was >99%.

Elementary Anal. Theor.: C: 73.0 H: 8.0 N: 2.8 O: 16.2
Found: C: 72.9 H: 8.1 N: 3.0 O: 16.5 j2) (−)-N,N-Diisopropyl-3-(2-hydroxy-5-hydroxymethylphenyl)-3-phenylpropylammonium (−) mandelate The title compound was obtained from (−)-N,N-diisopropyl-3-(2-benzyloxy-5-hydroxymethylphenyl)-3-phenylpropylamine in an analogous manner to that described in j1) above.

Elementary Anal. Theor.: C: 73.0 H: 8.0 N: 2.8 O: 16.2
Found: C: 73.2 H: 8.1 N: 3.0 O: 16.5

The free base had an optical rotation of $[\alpha]^{22}=-15.5°$ (c=5.0, ethanol).

The 1-(−)-mandelic acid salt had a m.p. of 147°–148° C. and an optical rotation $[\alpha]^{22}=-37.9°$ (c=4.7, methanol).

The optical purity as assessed by H.P.L.C. was >99%.

Pharmacology

Pharmacological tests performed with one compound of the invention and three prior art compounds disclosed in the above mentioned WO 89/06644 will now be described. The following compounds were used:

(A) (+)N,N-diisopropyl-3-(2-hydroxy-5-methylphenyl)-3-phenylpropylamine, hydrochloride (WO 89/06644);

(B) N,N-diisopropyl-3-bis-(2-hydroxyphenyl) propylamine hydrochloride (WO 89/06644);

(C) (+)N,N-diisopropyl-3-(5-chloro-2-hydroxyphenyl)-3-(2-hydroxyphenylpropylamine, hydrochloride (WO 89/06644);

(D) N,N-diisopropyl-3-(2-hydroxy-5-hydroxymethylphenyl)-3-phenylpropylamine (−) mandelic acid salt (Example 1 above).

Raised index numerals in the text below refer to literature references listed at the end of the description.

Muscarinic Receptor Binding Studies

The tissue preparations and the general methods used have been described in detail elsewhere for the parotid gland[1], urinary bladder[2], heart[3] and cerebral cortex[3], respectively. Male guinea pigs (250–400 g body weight) were killed by a blow on the neck and exsanguinated. The brain was placed on ice for dissection of the cerebral cortex (grey matter only). Urinary bladders, hearts and parotid glands were dissected in a Krebs-Henseleit buffer (pH 7.4) containing 1 mM phenyl methyl sulfonyl fluoride (PMSF, a protease inhibitor). Dissected tissues were homogenized in an ice-cold sodium-potassium phosphate buffer (50 mM, pH 7.4) containing 1 mM PMSF, using a Polytron PT-10 instrument (bladder, heart, parotid) and a Potter-Elvehjem Teflon homogenizer (cortex). All homogenates were finally diluted with the ice-cold phosphate/PMSF buffer to a final protein concentration of ≤0.3 mg/ml and immediately used in the receptor binding assays. Protein was determined by the method of Lowry et al. (1951)[4], using bovine serum albumin as the standard.

The muscarinic receptor affinities of the unlabelled compounds A to D identified above were derived from competition experiments in which the ability to inhibit the receptor specific binding of $(-)^3H$—QNB (1-quinuclidinyl[phenyl-4-$^3$H]benzilate, 32.9 Ci/mmole) was monitored as previously described[3,5]. Each sample contained 10 µl of $(-)^3H$—QNB (final concentration 2 nM), 10 µl solution of test compound and 1.0 ml tissue homogenate. Triplicate samples were incubated under conditions of equilibrium, i.e., at 25° C. for 60 minutes (urinary bladder), 80 minutes (heart and cerebral cortex) or 210 minutes (parotid gland), respectively. Non-specific binding was determined in the presence of 10 µM unlabelled atropine. Incubations were terminated by centrifugation[2], and the radioactivity in the pellets was determined by liquid scintillation spectrometry[2].

$IC_{50}$-values (concentration of unlabelled compound producing 50% inhibition of the receptor specific $(-)^3H$—QNB binding) were graphically determined from the experimental concentration-inhibition curves. Affinities, expressed as the dissociation constants $K_i$, were calculated by correcting the $IC_{50}$ for the radioligand-induced parallel shift and differences in receptor concentration, using the method of Jacobs et al. (1975)[6]. The binding parameters for $(-)^3H$—QNB ($K_D$ and receptor densities) used in these calculations were determined in separate series of experiments[1-3]. The $K_i$ values obtained for bladder, heart, parotid and cortex, respectively, are presented in Table 1 below.

Functional in vitro studies

Male guinea pigs, weighing about 300 g, were killed by a blow on the neck and exsanguinated. Smooth muscle strips of the urinary bladder were dissected in a Krebs-Henseleit solution (pH 7.4). The strip preparations were vertically mounted between two hooks in thermostatically controlled (37° C.) organ baths (5 ml). One of the hooks was adjustable and connected to a force transducer (FT 03, Grass Instruments). The Krebs-Henseleit solution was continuously bubbled with carbogen gas (93.5% $O_2$/6.5% $CO_2$) to maintain the pH at 7.4. Isometric tension was recorded by a Grass Polygraph (Model 79D). A resting tension of approximately 5 mN was initially applied on each muscle strip and the preparations were allowed to stabilize for at least 45 min. The resting tension was repeatedly adjusted and the preparations were washed several times during the stabilization period.

Carbachol (carbamylcholine chloride) was used as the standard agonist. In each experiment, the viability of the preparations and the reproducibility of their contractile responses were initially tested by three consecutive additions of a submaximal concentration ($3 \times 10^{-6}$M) of carbachol. A complete concentration-response curve to carbachol was then generated by cumulative addition of carbachol to the organ-bath (i.e., stepwise increase of the agonist concentration until the maximal contractile response was reached), followed by washing out and a resting period of at least 15 min. before a fix concentration of the test compound (antagonist) was added to the organ-bath. After 60 min. of incubation with the antagonist, a second cumulative concentration-response curve to carbachol was generated. Responses were expressed as percent of the maximal response to carbachol. $EC_{50}$-values for carbachol in the absence (control) and presence of antagonist were graphically derived and dose ratios (r) were calculated. Dissociation constants, $K_B$, for the antagonists were calculated using equation (1)[7], where [A] is the concentration of test compound.

$$K_B = [A]/r - 1 \quad (1)$$

The $K_B$ values obtained for compounds A, B and D identified above are shown in Table 1 below.

TABLE 1

| Test compound | $K_B$ nm bladder | $K_i$ nM bladder | $K_i$ nM heart | $K_i$ nM parotid | $K_i$ nM cortex |
|---|---|---|---|---|---|
| (A) | 3.0 | 2.7 | 1.6 | 4.8 | 0.8 |
| (B) |  | 10.2 | 6.7 | 2.6 | 1.5 |
| (C) | 2.6 | 2.5 | 0.9 | 2.7 | 0.4 |
| (D) | 4.1 | 4.5 | 0.9 | 4.7 | 0.7 |

Functional in vivo studies a) Animal preparation

Adult cats were anaesthetized with mebumal (42 mg/kg) intraperitoneally. When the animal was asleep, an infusion cannula was inserted into the foreleg vein and the cat was given alpha-chloralose. During the experiment the animal was placed on an operation table warmed up with a feedback controlled electric pad. The cat was tracheotomized. For blood pressure registration, a polyethylene catheter was inserted into the femoral artery, with the tip in aorta, and connected via a three-way stopcock to a blood pressure transducer and a Grass polygraph. Heart rate was registered by connecting a tachograph to a driver amplifier which received the signal from the blood pressure transducer. Blood flow in the central mesenteric artery was measured by an ultrasound flow probe around the artery connected to a transonic blood flow meter and then to a Grass polygraph for registration of the flow. For infusion of the test substances, compounds D and A (as identified above), a polyethylene catheter was inserted into the femoral vein three-way stopcock to a syringe placed in an infusion pump (Sage instrument).

Through an incision in the proximal urethra, a catheter was inserted into the urinary bladder. At the beginning of each experiment, this catheter was connected to an open vessel, which was filled with 38° C. tempered physiological saline and placed above the animal. During this stabilization period the bladder relaxed, leading to a filling of the bladder with saline, under constant hydrostatic pressure. After the stabilization period, the bladder catheter was connected to a pressure transducer, for registration of intravesical pressure. Blood pressure, heart rate, blood flow and bladder pressure were recorded simultaneously and continuously throughout the experiment. The animals were left for at least 45 minutes to achieve steady state in cardiovascular variables before starting the experiment.

Bladder pressure was measured at 8 minutes after the end of infusion of the test substance. The surgical preparation was tested by intravenous injection of 0.25 µg/kg b.w. of noradrenalin and 0.5 µg/kg b.w. of acetylcholine.

b) Dosing

To study the dose-response relationship of compound D identified above, the substance was administered at the doses 0.000 (physiological saline), 0.003, 0.010, 0.030 and 0.100 mg/kg, respectively, with infusion during 2 minutes and an infusion volume of 1 mL/kg. Every cat got all doses and was left to reestablish at least 45 minutes between the 0.003 and 0.010 mg/kg doses, and 60 minutes between the 0.030 and 0.100 mg/kg doses.

c) Statistical methods and calculation

The results are presented in absolute values and calculated as mean value±standard deviation d) Results (i) Blood pressure In general, intravenous administration of compound D had little or no effect on the blood pressure except at dose of 0,3 mg/kg. This dose caused an increase with 10% and with 6% for diastolic blood pressure and systolic blood pressure, respectively.

(ii) Blood flow

Intravenous administration of compound D caused an increase with 8, 17 and 21% of the blood flow in superior mesenterica artery at 0.003, 0.01, and 0.03 mg/kg, respectively. Again at the highest dose (0.3 mg/kg) a 10% increase in blood flow was observed.

(iii) Heart rate

Intravenous administration of compound D caused a decrease with 9% at the highest dose (0.3 mg/kg).

(iv) Bladder pressure

As appears from FIG. 1, compound D of the present invention produced a dose-dependent inhibition of the acetylcholine-induced effect on the bladder which was about ten times more efficient than that of prior art compound A.

References

1. Nilvebrant, L.; Sparf, B. Muscarinic receptor binding in the parotid gland. Different affinities of some anticholinergic drugs between the parotid gland and ileum. Scand. J. Gastroenterol. 1982, 17 (suppl. 72), 69–77.
2. Nilvebrant, L.; Sparf, B. Muscarinic receptor binding in the guinea pig urinary bladder. Acta Pharmacol. et Toxicol. 1983 a, 52, 30–38.
3. Nilvebrant, L; Sparf, B. Dicyclomine, benzhexol and oxybutynin distinguish between sub-classes of muscarinic binding-sites. Eur. J. Pharmacol. 1986, 123, 133–143.
4. D Lowry, O. H.; Rosebrough, N. J.; Farr, A. L.; Randall, R. J. Protein measurement with the Folin phenol reagent. J. Biol. Chem. 1951, 193, 265–275.
5. Nilvebrant, L.; Sparf, B. Differences between binding affinities of some antimuscarinic drugs in the parotid gland and those in the urinary bladder and ileum. Acta Pharmacol. et Toxicol. 1983 b, 53, 304–313.
6. Jacobs, S.; Chang, K.-J.; Cuatrecasas, P. Estimation of hormone receptor affinity by competitive displacement of labelled ligand. Effects of concentration of receptor and labelled ligand. Biochem. Biophys. Res. Commun. 1975, 66, 687–692.
7. Schild, H. I. pAx and competitive drug antagonism. Br. J. Pharmacol. Chemother. 1949, 4, 277–280.

What is claimed is:

1. A 3 3-diphenylpropylamine of the formula I:

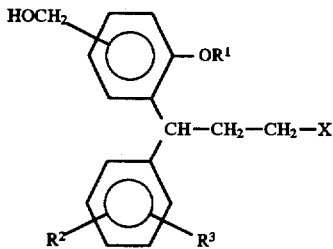

wherein $R^1$ represents hydrogen or methyl, $R^2$ and $R^3$ independently represent hydrogen, methyl, methoxy, hydroxy, carbamoyl, sulphamoyl or halogen, and X represents a tertiary amino group of formula II $$-N\begin{matrix}R^4\\R^5\end{matrix} \quad \text{II}$$

wherein $R^4$ and $R^5$ independently represent a hydroxy substituted or unsubstituted non-aromatic hydrocarbyl group which can join together to form a ring and which together contain at least three carbon atoms, wherein at least one of $R^4$ and $R^5$ is hydroxy substituted; or a physiologically acceptable acid salt thereof.

2. The 3,3-diphenylpropylamine according to claim 1 wherein $R^4$ and $R^5$ are each independently saturated hydroxy substituted or unsubstituted hydrocarbyl groups.

3. The 3,3 -diphenylpropylamine according to claim 1, wherein the $HOCH_2$-group is in the 5-position on the phenyl ring, $R^2$ is hydrogen and $R^3$ is hydrogen or hydroxy.

4. A pharmaceutical composition comprising an effective amount of a 3,3-diphenylpropylamine according to claim 1 and a compatible pharmaceutical carrier.

5. The 3,3-diphenylpropylamine according to claim 1, wherein said compound is an individual enantiomer.

6. The 3 3-diphenylpropylamine according to claim 2, wherein $R^4$ and $R^5$ independently represent a hydroxy substituted or unsubstituted $C_{1-8}$-alkyl group or adamantyl and the total number of carbon atoms contained in $R^4$ and $R^5$ is at least four carbon atoms.

7. The 3,3-diphenylpropylamine according to claim 6, wherein $R^4$ and $R^5$ independently represent a hydroxy substituted or unsubstituted $C_{1-6}$-alkyl group.

8. The 3,3-diphenylpropylamine according to claim 3, wherein $R^3$ is in the 2-position on the phenyl ring.

9. A method for treating acetylcholine-mediated disorders which comprises administering to a patient in need thereof an effective amount of a 3,3-diphenylpropylamine as claimed in claim 1.

10. The method according to claim 9, wherein said disorder is urinary incontinence.

* * * * *